United States Patent [19]
Nexo et al.

[11] 4,236,075
[45] Nov. 25, 1980

[54] APPARATUS FOR MEASURING COMPONENTS OF LIQUID SAMPLES

[75] Inventors: Sten A. Nexø, Birkerød; Andreas S. Frandsen, Slangerup, both of Denmark

[73] Assignee: A/S N. Foss Electric, Hillerød, Denmark

[21] Appl. No.: 931,621

[22] Filed: Aug. 7, 1978

[51] Int. Cl.² .............................................. G01J 1/00
[52] U.S. Cl. ..................................... 250/343; 250/351
[58] Field of Search ....................... 250/343, 347, 351

[56] References Cited

U.S. PATENT DOCUMENTS

| | | | |
|---|---|---|---|
| 2,775,160 | 12/1956 | Foskett et al. | 250/343 |
| 3,939,348 | 2/1976 | Barrett | 250/343 |
| 4,100,412 | 7/1978 | Hausdorff | 250/343 |

*Primary Examiner*—Alfred E. Smith
*Assistant Examiner*—Janice A. Howell
*Attorney, Agent, or Firm*—Dennison, Dennison, Meserole & Pollack

[57] ABSTRACT

An apparatus for measuring components of liquid samples, such as milk samples, based on the ability of these components to absorb infrared radiation at certain frequencies. A single radiation beam is directed through a cuvette containing the sample, and the apparatus comprises a plurality of pairs of optical filters. Each of these pairs is associated with a respective one of the components to be measured and comprises a component filter for passing infrared radiation at a narrow frequency band at which the radiation absorbing ability of the said component is relatively high, and a reference filter for passing infrared radiation at a different narrow frequency band at which the radiation absorbing ability of the component is lower. A component of the sample is measured by successively positioning the filters of the associated pair of filters in the radiation beam between the radiation source and the cuvette, and the radiation passing the cuvette is detected by a detector, preferably a thermopile radiation detector of the monolithic type, and the content of the respective component is calculated on the basis of the signals received from the detector. The radiation beam is chopped by means of conventional chopping means, and each of the filters is preferably retained in the radiation beam in a period of time comprising a plurality of cycles of the chopping means.

42 Claims, 8 Drawing Figures

APPARATUS FOR MEASURING COMPONENTS OF LIQUID SAMPLES

BACKGROUND OF THE INVENTION

1. Field of the Invention

The present invention relates to an apparatus for measuring components of liquid samples based on the ability of these components to absorb infrared radiation at certain frequencies. The apparatus according to the invention which may be used for analyzing liquid samples in general is specifically, but not exclusively, intended for use in analyzing liquid milk samples or determining components thereof.

2. Description of the Prior Art.

Analyzing apparatuses for automatic determination and registration of various components, such as fat, protein, and lactose, of milk samples being exposed to infrared radiation, are known. In such known apparatus infrared radiation from a radiation source is divided into two separate beams which by means of a system of mirrors are passed through a component filter and a reference filter, respectively. The component filter admits a narrow band of infrared wave lengths at which the radiation absorbing ability of the component to be measured is relatively high, and the reference filter admits a narrow band of wave lengths at which the radiation absorbing ability of said component is substantially lower. These filtered infrared radiation beams are interrupted by a rotating reflecting chopper disc at a frequency of 12.5 Hz, and the component and reference light pulses thus generated are directed through a transparent cuvette containing the milk sample and thereafter focused on a pyroelectric radiation detector which generates an electric signal in response to the radiation pulses received. A radiation attenuating comb-like member extends into the reference beam and may be displaced by a DC servomotor which is energized by the electrical signal from the radiation detector. When unbalance of the sample and reference beams occurs because of a change in sample component absorption the amplified signal causes the servomotor to drive the attenuating comb-member further into or out of the reference beam until balance is restored. The component of the sample is then determined as a function of the position of the comb-like member in the reference beam when balance has been obtained.

The known analyzing apparatus with the dual beam system described above is of a rather complicated structure containing ten different mirrors the positions of which must be accurately adjusted. Furthermore, the accuracy of a dual beam system implies i.a. that the condition of the beam directing mirrors associated with each of the two beams does not change non-uniformly, for example due to dust or other changes in reflection ability.

The prior art also comprises an infrared single beam analyzer for determining one component of a gas flowing through a transparent gas cell. An infrared radiation beam is directed from an infrared source through the gas cell by means of optical lenses and focused on an indium antimonide detector. The radiation beam is chopped at a chopping frequency of 600 Hz, and interference filters selected for the measurement and reference wave lengths are interposed alternately in the radiation beam at a frequency at about 6 Hz so that the detector receives chopped energy at a level corresponding alternately to the measurement and reference transmission levels. Consequently, the output signal of the detector is a 600 Hz carrier modulated at 6 Hz. The signal generated by the detector is supplied to signal processing circuits for determining the component to be measured on the basis of said signal.

SUMMARY OF THE INVENTION

The present invention provides a simplified infrared analyzing apparatus of the single beam type for determining a plurality of components of a liquid sample. The apparatus according to the invention comprises a source of infrared radiation, transparent sample receiving means, means for directing a beam of radiation from said source through said sample receiving means, means for chopping said beam at a predetermined frequency at a position between said source and said sample receiving means, a plurality of pairs of optical filters, each of said pairs being associated with the respective one of said components and comprising a component filter for passing infrared radiation at a narrow frequency band at which the radiation absorbing ability of said component is relatively high, and a reference filter for passing infrared radiation at a different narrow frequency band at which the radiation absorbing ability of said component is low, means for successively positioning said filters of at least one pair in said radiation beam between said source and said sample receiving means and for maintaining each filter in said radiation beam during a plurality of cycles of said chopping means, a thermopile radiation detector arranged so as to receive radiation having passed said sample receiving means and for providing signals in response thereto, and means for calculating values of said components on the basis of said signals.

Compared to the known liquid sample analyzing apparatus described above the apparatus according to the invention is of a mechanically simple, rugged, and compact structure. In the apparatus according to the invention only one radiation beam is used, and consequently, the optical alignment of the beam directing means of the apparatus is simple and uncritical. Furthermore, the influence of the amount of water vapour present is reduced and possible mechanical distortion of the casing surrounding and protecting the beam directing means and the apparatus parts associated therewith will not substantially affect the measurements of the apparatus. The thermopile radiation detector used in the apparatus according to the invention is a robust wide-range detector rendering it possible to determine a desired number of different components of the liquid sample being measured.

The said thermopile detector is preferably of the monolithic type whereby "microphone effect" is avoided so as to make the apparatus less sensitive to shocks and vibrations.

The apparatus according to the invention may be used for determining components of any type of liquid sample which may be analyzed by infrared spectrometry. A preferred embodiment of the apparatus is, however, adapted to analyze samples of liquid milk products, and in that case the frequency bands of said filters are preferably within the frequency range $4.5\mu-10\mu$.

Although the apparatus according to the invention is of the type in which one and the same radiation beam is used for generating the component signal as well as the reference signal, that beam may be directed along a tortuous path by means of suitable reflecting means such as mirrors. However, it is preferred to arrange the radiation source, the sample receiving means, and the detector so that they are aligned in order to obtain a simplified structure. The radiation beam may then be focused on the sample receiving means and on the detector, respectively, by means of only two lenses or concave mirrors. In the known apparatuses described above the radiation detector must generate several alternating component and reference signals for each component to be determined. According to the present invention the said filter positioning means are preferably adapted to retain each filter of a pair of filters in the single radiation beam in a period of time exceeding 0.5 seconds and in many cases even 1.5 seconds in order to give the thermopile detector sufficient time to detect the intensity of the radiation passing each filter and to generate a signal in response thereto. The calculating means of the apparatus may then be adapted to calculate a value of the component associated with the pair of filters used on the basis of only two such consecutive signals, namely one reference signal and one component signal.

It may be found necessary to retain each filter in the radiation beam in a still longer period of time, for example 4.7 seconds or even more.

Due to the long residence time of each filter in the radiation beam it is important that the conditions of the elements of the apparatus and of the surroundings, such as temperature and moisture conditions, do not change to any appreciable degree in the period of time in which each pair of filters including a measuring filter and a corresponding reference filter is placed in the radiation beam for measuring one component of a sample. In order to prevent any radiation from the chopping means from influencing the detector these chopping means are preferably arranged between the radiation source and the filters. The temperature of the filters may be controlled by independent temperature control means in order to keep the optical characteristics thereof substantially constant.

The detector may generate signals which are representative of the amounts of radiation energy $E_c$ and $E_r$ received in the periods of time in which the component filter and the reference filter, respectively, of a pair of filters are positioned in the radiation beam. The value C of the component may then be calculated on the basis of the following expression $$(E_c/E_r)\beta - \alpha_o$$

wherein $\beta$ and $\alpha_o$ are predetermined constants, such as apparatus constants determined by calibration of the apparatus. Preferably, $\alpha_o$ is an arbitrarily fixed constant while $\beta$ is determined so as to make the expression zero when the sample is pure water.

The apparatus according to the invention comprises a plurality of pairs of optical filters so that it is able to measure the content of two or more components in a liquid sample. However, in some cases it is desired to determine only one or some of the components which may be measured by means of the apparatus. Therefore, in a preferred embodiment the apparatus comprises filter selecting means for selecting one of a predetermined number of combinations of said plurality of filter pairs to be used for measuring selected components of a sample positioned in said sample receiving means and for controlling the function of said filter positioning means in correspondence with the selection made by the user of the apparatus.

The filters may be arranged on a filter support rotatable about an axis substantially parallel with the longitudinal axis of the beam. It is then possible to change the filter position in the radiation beam merely by rotating the filter support. One or more of the filters may be mounted adjustably on the support so that the angle defined between the axis of the support and the plane of said filter may be changed. By changing the inclination of the filter it is possible to change the distance traversed by the radiation beam through the filter, and thereby the frequency band or center wavelength of the filter may be changed slightly.

In known infrared milk analyzers the radiation beams emitted from the radiation source are restricted to a relatively small aperture angle. It has been found, however, that the negative influence of the inevitable scattering of the radiation beam may be reduced by increasing the aperture angle. Therefore, the beam directing means may define between said sample receiving means and said second mirror a radiation beam diverging at an angle of 20°–45°, preferably 30°–40°.

According to another aspect of the invention the apparatus for measuring components of a liquid sample may comprise a source of infrared radiation, transparent sample receiving means, means for directing one beam of radiation from said source through said sample receiving means, means for chopping said beam at a predetermined frequency and at a position between said source and said sample receiving means, a plurality of pairs of optical filters, each of said pairs being associated with a respective one of said components and comprising a component filter for passing infrared radiation at a narrow frequency band at which the radiation absorbing ability of said component is relatively high, and a reference filter for passing infrared radiation at a different narrow frequency band at which the radiation absorbing ability of said component is low, means for successively positioning said filters of at least one pair in said radiation beam between said source and said sample receiving means and for maintaining each component filter and each reference filter in said radiation beam in a period of time comprising a plurality of cycles of said chopping means, a radiation detector arranged so as to receive radiation having passed said sample receiving means and for providing a pulsed component signal in response to radiation received through the component filter of a pair of filters in one such period of time, and for providing a pulsed reference signal in response to radiation received through the reference filter of said pair in another such period of time, and means for calculating a value of a component on the basis of said measuring and reference signals.

The said calculating means may comprise a variable gain amplifier, means for passing said reference signal to the input of the amplifier, means for varying the gain of said amplifier to a level at which the amplified reference signal corresponds to a predetermined value, means for maintaining the gain of the amplifier substantially at said level, and means for passing said components signal to the input of the amplifier while the gain thereof is kept at said level. The amplified component signal will then represent the said predetermined value multiplied by the ratio of the component signal to the reference signal. The structure described may, for example, be used for calculating the expression $$(E_c/E_r)\beta - \alpha_o$$

The calculating system described may, however, be used for calculating the ratio between any two voltage signals.

The said gain varying means may comprise a radiation sensitive resistor, such as a photoresistor connected to the input of said amplifier, and a radiation emitting device or light source, such as a light emitting diode, controlled by the output of said amplifier. The said gain maintaining means may comprise a memory connected to the output of said amplifier and to said radiation emitting device, and a switching device which may, for example, be controlled by an electronic control system of the apparatus, for disconnecting said amplifier while said component signal is being passed to said amplifier.

BRIEF DESCRIPTION OF THE DRAWINGS

The invention will now be further described with reference to the drawings, wherein.

DESCRIPTION OF THE PREFERRED EMBODIMENT

Figure 1:
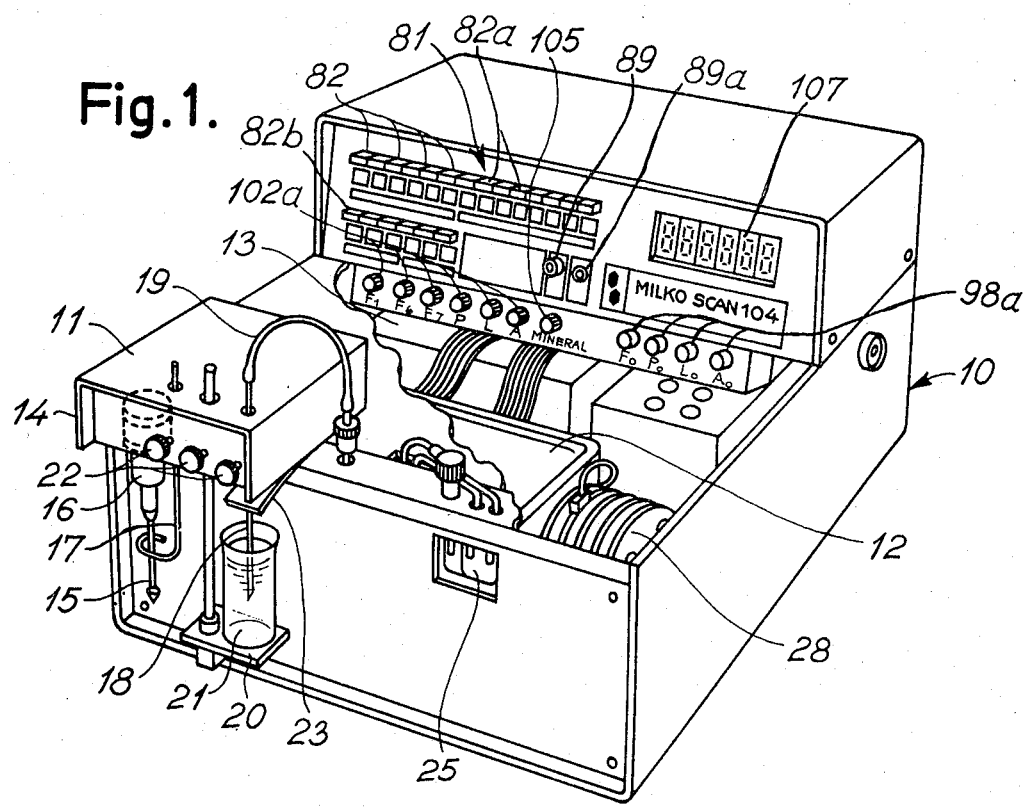
FIG. 1 is a perspective view of an embodiment of the apparatus according to the invention, certain wall parts having been removed.

FIG. 1 shows a milk analyzing apparatus 10 for determining the content of one or more of the components fat, protein, lactose, and water in a milk sample. The apparatus is also able to determine the total content of solids and of solids other than fat in the sample. The apparatus 10 comprises a sample intake unit 11, an optical unit 12, and an electronic control unit 13.

The sample intake unit 11 includes a supporting bracket 14 supporting a stirrer 15 which is driven by an electric motor 16. The motor 16 is energized by means of a microswitch (not shown) which may be activated by an activating member 17 arranged adjacent to the stirrer. The bracket 14 also supports a pipette 18 connected to the optical unit 12 by means of a flexible tube or hose 19, and a support 20 for supporting a cup 21 containing a sample to be analyzed is suspended below the lower free end of the pipette 18. The vertical positions of the activating member 17, the pipette 18, and the cup support 20 may be adjusted by means of adjusting screws 22. A microswitch (not shown) for starting the measuring procedure may be activated by means of an activating arm 23 arranged adjacent to the pipette 18.

Figure 2:
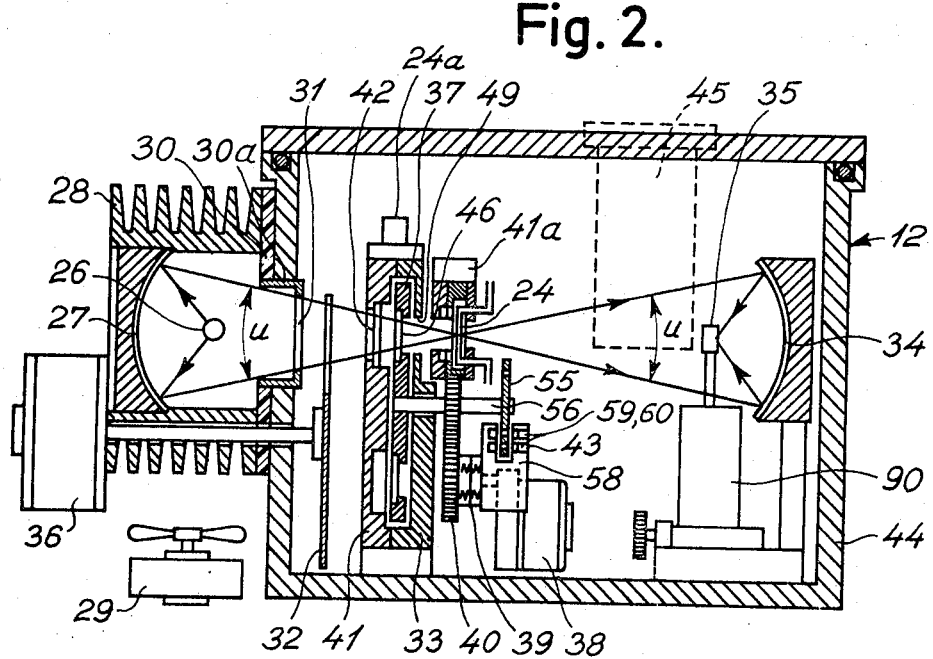
FIG. 2 is a diagrammatic sectional view of an optical unit of the apparatus shown in an enlarged scale.

The actual measurement of the sample takes place within the optical unit 12 containing a cuvette 24 in which the milk sample flows as a thin film between two closely spaced transparent plates. These plates may, for example, be made from calcium fluoride having a spacing of about 37μ. The temperature of the cuvette 24 is preferably thermostatically controlled as indicated by 24a so as to maintain the temperature at a substantially constant value, for example at 40° C. The cuvette 24 communicates with a pipette 18 and with a discharge container 25 as described more in detail below. The optical unit 12 also comprises an infrared radiation source 26 fed by a stabilized electricity supply so as to keep the energy radiated by the infrared source substantially constant. The infrared source may, for example, be a platinum filament moulded into a porcelain tube. A concave mirror 27 reflects the infrared radiation so as to substantially focus a beam of radiation on the cuvette 24 as indicated in FIG. 2. The radiation source 26 and the mirror 27 are mounted within a tubular housing 28 provided with outer coding fins, and a blower 29 generates a flow of cooling air for cooling the housing 28. A heat insulating plate 30, which may, for example, be made from polyvinyl chloride and a tubular member 30a mounted therein form an end wall of the housing 28 opposite to the mirror 27 and defines an aperture 31. The aperture angle $\mu$ is preferably relatively big, for example 36°, for reasons described below. The radiation beam leaving the aperture 31 passes a chopper disc 32 and a filter unit 33 and hits a second concave mirror 34 focusing the radiation on a radiation detector 35 which is preferably a thermopile detector of the monolithic type "Type S 15 Thermopile Detector" produced by Sensors Inc., Michigan. The chopper disc 32 is driven by an electric motor 36 and at constant rotational speed, for example at 10 revolutions per minute. The motor 36 may be a step motor operating at 20 steps per minute and energized by a non-varying electricity source, for example a generator, not shown. The chopper disc 32 is of such a shape that the radiation beam is chopped once for each revolution of the disc, and the time periods in which the beam is interrupted by the chopper disc 32 are preferably of the same duration as the time periods in which the radiation beams passes uninterrupted.

The filter unit 33 includes a rotatable filter change wheel 37 which may be driven by an electric motor 38 through a coupling 39 and gears 40. The motor 38 may, for example, be a synchronous gear motor operating at 10 revolutions per minute. The filter change wheel 37 is located within a filter housing 41 the temperature of which is thermostatically controlled as indicated by 41a so as to maintain the temperature in the filter housing 41 substantially constant. The chopped infrared radiation beam passes through a heat filter 42 mounted in the stationary filter housing 41 and through one of a plurality of optical filters mounted on the filter change wheel 37. The filter unit 33 further includes a filter code device 43 for selecting the filter to be aligned with the radiation beam as described more in detail below. The chopper disc 32, the filter unit 33, the mirror 34, and the radiation detector 35 are mounted within a sealed, gastight box or housing 44 in which the atmosphere may be kept in a dry condition by means of a replaceable cartridge 45 containing silica gel or another air drying substance.

Figure 3:
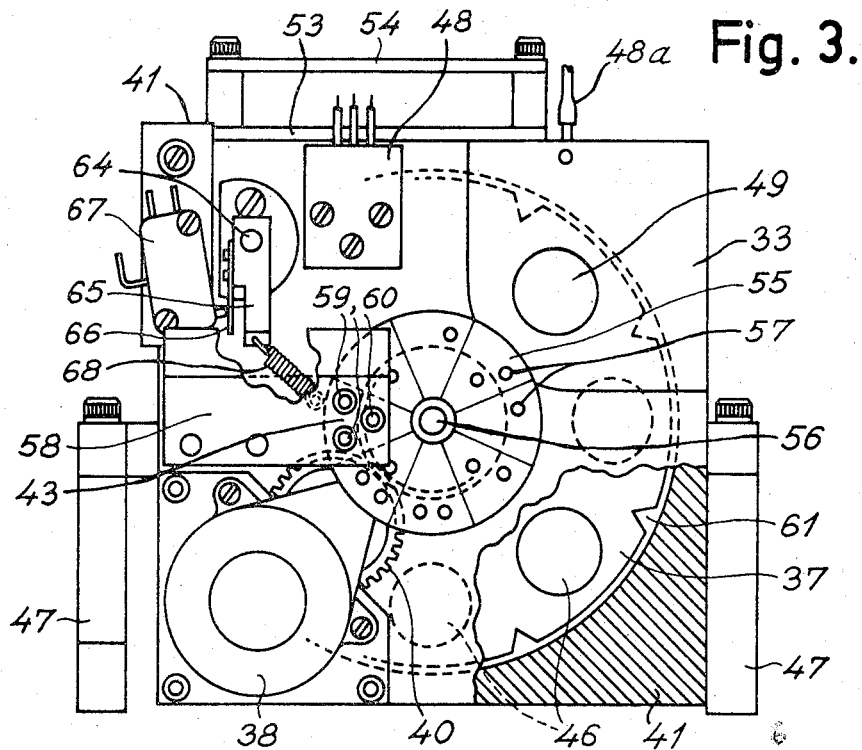
FIG. 3 is a side view of a filter unit of the apparatus, certain wall parts having been removed.
Figure 4:
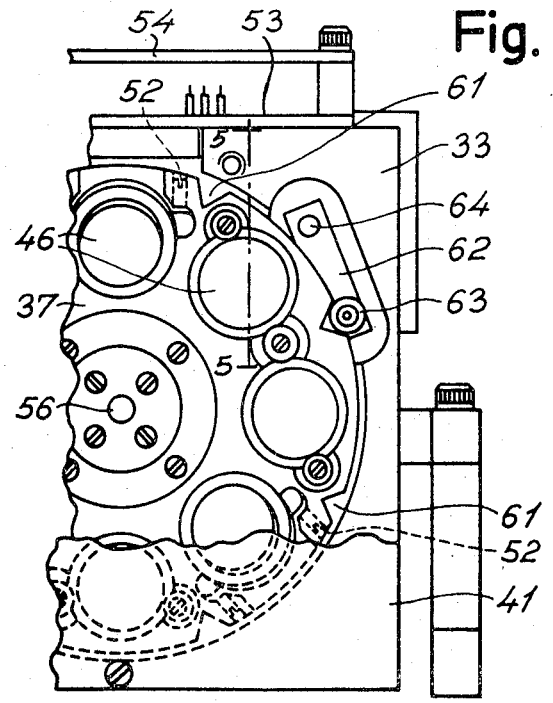
FIG. 4 is part of the filter unit shown in FIG. 3 and viewed from the opposite side.
Figure 5:
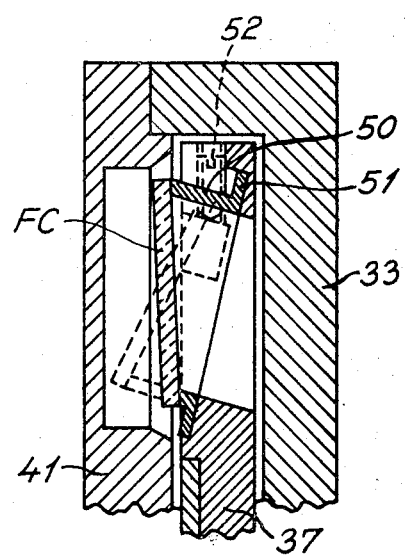
FIG. 5 is a sectional view 5—5 as indicated in FIG. 4.

The filter unit 33 will now be described more in detail with special reference to FIGS. 3–5. The filter change wheel 37 is provided with eight optical filters 46 arranged uniformly spaced along a circle having its center on the axis of the wheel. The eight filters 46 comprise four pairs of filters, each pair including a component filter admitting a narrow band of infrared wave lengths at which radiation absorbing ability of the component to be measured is relatively high, and a reference filter admitting a narrow band of wave lengths at which the radiation absorbing ability of said component is substantially lower. The filters 46 comprise a reference filter FR and a component filter FC for measuring fat, a reference filter PR and a component filter PC for measuring protein, a reference filter LR and a component filter LC for measuring lactose, and a component filter WC and a reference filter WR for measuring water in a milk sample. The filters for measuring fat, protein, and lactose are preferably of the same type as those used in a known milk sample analyzer sold under the tradename "Milko-Scan 203" by A/S N. Foss Electric, Hillerød, Denmark. The housing 41 in which the filter change wheel 37 is rotatably mounted is provided with supporting brackets 47 by means of which the filter unit is connected to the bottom of the box or housing 44 in such a position that the heat filter 42 (FIG. 2) is aligned with the radiation source 26, the cuvette 24, and the radiation detector 35. The heat filter 42 which is provided for protecting the filter housing from undue heating is preferably of a type cutting off radiation with wave lengths smaller than 4.3μ. As indicated above the filter housing 41 is thermostatically controlled so as to maintain a substantially constant temperature of the filters well about normal ambient temperature, for example at 41° C. For that purpose the filter housing may be made from a heat conductive material, such as aluminum, and provided with a power transistor 48 which is controlled by a thermistor 48a so as to maintain the temperature at the desired level. In order to allow the radiation beam emitted by the radiation source 26 to pass through the filter unit the wall part of the filter housing 41 opposite to the heat filter 42 defines a beam outlet opening 49 aligned with the heat filter 42 and the cuvette 24.

One or more of the filters 46 preferably the component filter FC for measuring fat and the component filter WC for measuring water are adjustably mounted on the filter change wheel 37 so that the inclination of the filters FC and WC in relation to a plane normal to the axis of the radiation beam emitted by the radiation source 26 may be varied, for example within the range 5°-30°. As shown in FIG. 5 the filter FC is fastened to an annular filter holder 50 with a flange 51 defining an abutment surface which forms an acute angle of for example 12.5°. In the mounted position of the filter this abutment surface engages with a corresponding oblique surface part forming the bottom surface of an annular recess in the filter change wheel 37 receiving the flange 51 of the holder 50. The filter holder 50 may be fixed to the filter change wheel 37 by means of screws 52 or other suitable releasable fastening means. At its upper end the filter housing 41 is provided with a removable lid 53 having a hand grip 54. When the inclination of the filter FC shown in FIG. 5 is to be changed, the lid 53 is removed, and the filter change wheel 37 is rotated to a position in which the filter holder 50 is accessible through the opening provided by removal of the lid 53. When the screws 52 have been loosened the holder 50 and the filter FC fastened thereto may be turned till the desired oblique position has been obtained, whereafter the holder 50 may be secured in the new position by tightening of the screws 52. In FIG. 5, different positions of the holder 50 are indicated in solid and broken lines, respectively. By changing the inclination of the filter it is also possible to change the effective thickness of the filter which means the transversing distance of the radiation beam through the filter and thereby the center wavelength.

The filter code device 43 comprises a code disc 55 mounted on the shaft 56 of the filter change wheel 37 outside the filter housing 41. The code disc 55 which is of an opaque material is divided into eight sectors corresponding to the eight filters of the filter change wheel 37, and each sector of the code disc 55 is provided with the three first digits of a 4-bit digital code, and each of these codes represents a corresponding one of the filters 56. In the embodiment shown on the drawings the digital codes are composed by throughgoing holes 57 in the code disc 55. The filter code device 43 further comprises a code reading device including a fork-shaped block 58 which is preferably of a opaque material and which embraces the code disc 55 as best shown in FIG. 2. One leg of the fork-shaped block 58 supports three light sources such as light emitting diodes 59 and the other leg supports oppositely directed photoelectric devices such as phototransistors 60. The diodes 59 and the phototransistors 60 are positioned so that they may become aligned with the holes 57 in any sector of the code disc 55. A mechanical locking device is adapted to lock the filter change wheel 37 in any of eight angular positions in which the light emitting diodes 59 and the phototransistors 60 register with the holes 57 of a digital code of the code disc 55. This mechanical locking device comprises eight notches 61 which are formed in the rim portion of the filter change wheel 37 and uniformly circumferentially spaced. A locking arm 62 having a roller 63 mounted at its free end is swingably mounted by means of a shaft 64 extending transversely through the filter housing 41. An arm 65 mounted at the opposite end of the shaft 64 carries a switch actuating spring member 66 which may actuate a microswitch 67. A spring 68 connected to the arm 65 tends to swing the arm 65 and the locking arm 62 in a direction so as to press the roller 63 into contact with the outer periphery of the filter change wheel 37. When the wheel 37 is rotated by the motor 38 to a position in which the roller 63 engages with one of the notches 61 the actuating will actuate the microswitch 67 which then provides the fourth bit of the above mentioned digital code.

Figure 6:
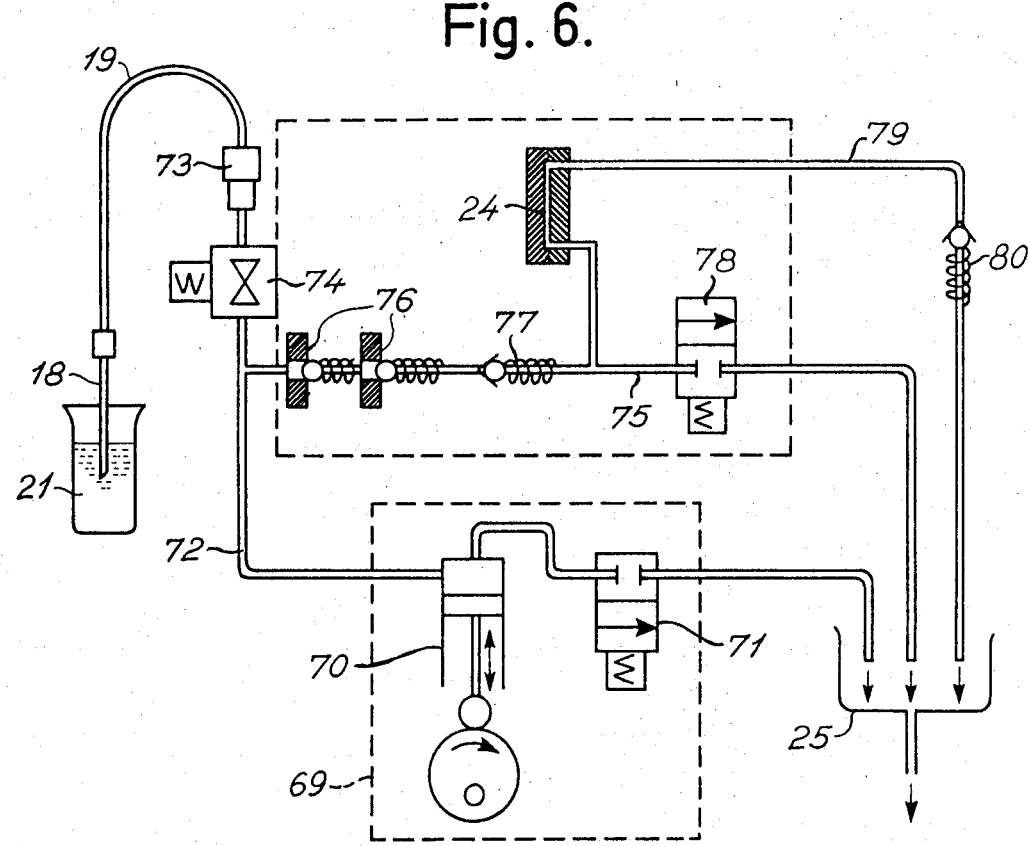
FIG. 6 is a sample flow diagram.

The flow of a milk sample through the apparatus will now be described with reference to FIG. 6. The apparatus shown in FIG. 1 is normally used in connection with a high pressure pump unit 69 which may, for example, be of a known type used in connection with the above mentioned milk sample analyzer sold under the tradename "Milco-Scan 203" by A/S N. Foss Electric, Hillerød, Denmark. The unit 69 comprises a high pressure pump 70 and an electrically controlled bleeder valve 71 through which the pump cylinder is connected to the discharge 25. The pipette 18 and the hose 19 are connected to the high pressure pump unit 69 through a conduit 72 including a milk filter 73 and an electrically controlled intake valve 74. A conduit 75 branched off from the conduit 72 includes a double ball valve homogenizer 76 of known type, a normal one-way valve 77 and an electrically controlled by-pass valve 78. A further conduit 79 is branched off from the conduit 75 between the one-way valve 77 and the by-pass valve 78. The conduit 79 includes the cuvette 24 and a one-way valve or a back-pressure valve 80. The conduits 75 and 79 both open into the discharge 25.

When the pump 70 is started as explained below it will be driven through seven full strokes before it is stopped. During each of the suction strokes of the first four full strokes an amount of milk sample (for example 1.5 ml) is sucked from the sample cup 21 through the pipette 18, the hose 19, the milk filter 73, and the intake valve 74 into the conduit 72, the valves being controlled so that the valve 71 is closed, while the intake valve 74 is open. During the main part of each of the pressure strokes of said first four full strokes the intake valve 74 is closed while the valve 71 is open so that milk sample is pumped through the conduit 72 to discharge 25. However, before completion of each of said pressure strokes the valve 71 is closed so that part of the milk sample is pumped through the homogenizer 76, the conduit 75, and the by-pass valve 78 which is open. Therefore, during the first four full strokes remains of a preceding sample are flushed out from the conduits 72 and 75 (but not the conduit 79 and the cuvette 24) into the discharge 25.

During each of the following two (the fifth and sixth) pressure strokes of the pump 70 the bleeder valve 71 remains closed so that the milk sample is pumped through the homogenizer 76 at a high pressure, for example about 90 kg/cm$^2$. During the first part of each of the fifth and sixth pressure strokes the by-pass valve 78 is open so that the major part (for example 1.3 ml) of the homogenized milk sample pumped in each stroke is passed to waste 25 through the conduit 75. Almost at the end of each of the said fifth and sixth pressure strokes the by-pass valve 78 is closed so that a minor part (for example 0.2 ml) of the homogenized sample of each stroke is flushed through the cuvette 24, the conduit 79, and the back pressure valve 80 to waste 25, leaving a few microliters of clean homogenized sample in the cuvette 24 for measurement after completion of the sixth pressure stroke. The back pressure valve 80 secures that a substantially constant pressure (for example 1.5 kg/cm$^2$ above that of the atmosphere) is maintained during the measuring period. During the seventh suction stroke of the pump 70 the intake valve 74 remains closed while the bleeder valve 71 is opened. Consequently, the volume of milk sample residing in the conduit extending between the pump 70 and the discharge 25 (for example about 1.5 ml) is sucked back into the pump 70 and during the seventh pressure stroke the bleeder valve 71 is closed while the intake valve 74 is opened whereby milk sample is pumped back through the intake valve and the milk filter 73 into the sample cup 21 in order to rinse and remove possible impurities from the filter 73.

As indicated above, in the presently preferred embodiment about 1.5 ml of milk is removed from the sample cup 21 during each of the first six suction strokes while about 1.5 ml is returned to the cup 21 during the seventh and last pressure stroke.

Figure 7:
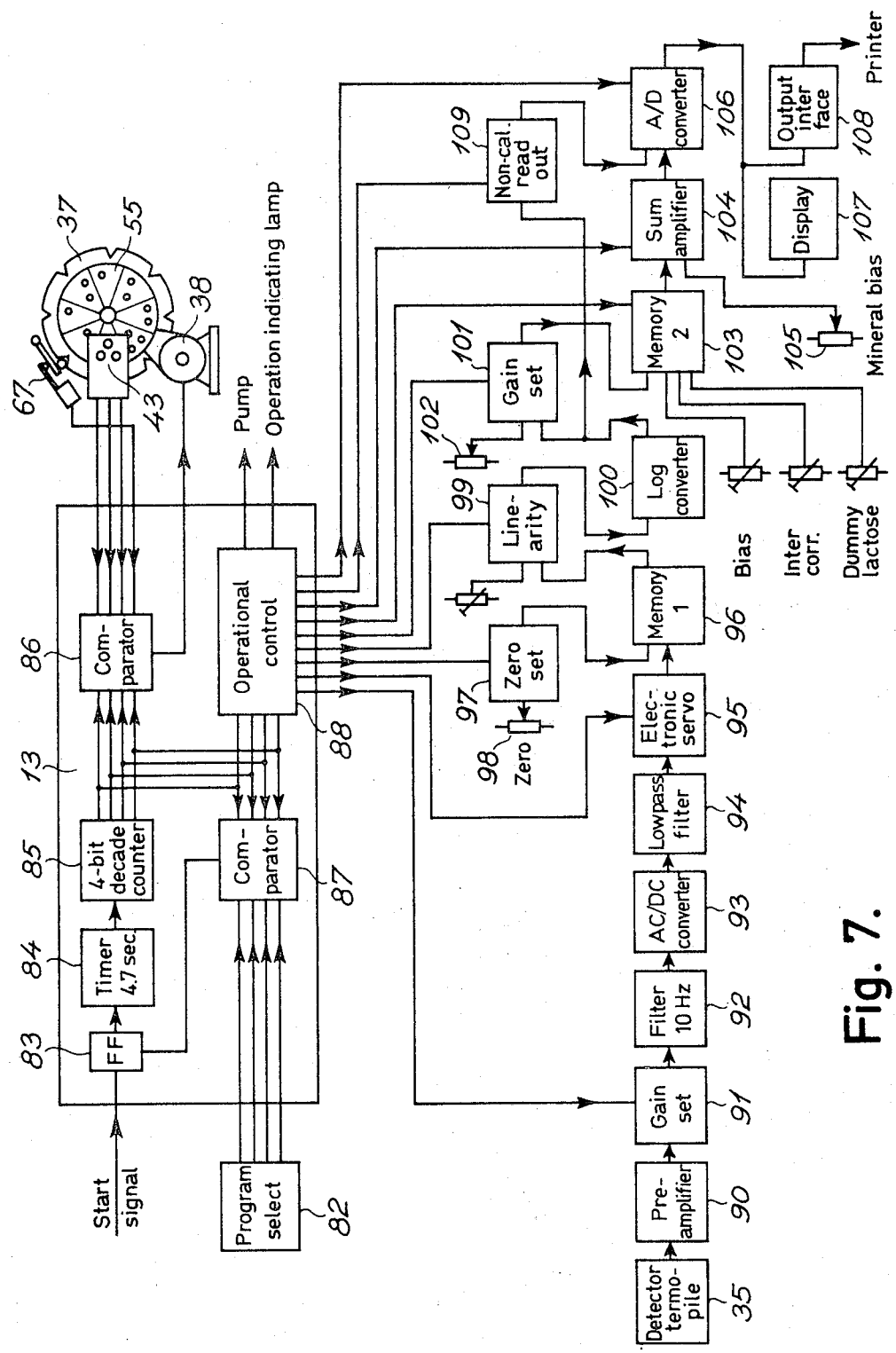
FIG. 7 is a block diagram of the electronic system of the apparatus.

The function of the above apparatus will now be explained more in detail with special reference to the block diagram of the electronic system shown in FIG. 7. The apparatus shown in FIG. 1 has a keyboard 81 with a number of program-selecting push buttons 82 by means of which the user of the apparatus may select a desired program, i.e. a desired combination of components in the milk sample to be measured, such as fat and protein—fat, protein, and lactose—fat, protein, lactose, and water—fat, protein, and total solids—fat, protein, and solids which are not fat. The cup 21 containing the sample to be measured may now be positioned below the stirrer 15, and by moving the cup 21 upwardly into contact with the activating member 17 the motor 16 may be energized. When the sample has been sufficiently stirred the sample cup 21 is moved to a position below the pipette 18, and the cup is moved upwardly in order to actuate the start switch activating arm 23. Thereafter the cup may be supported by the support 20 as shown in FIG. 1. Activation of the start switch by means of the arm 23 provides a start signal which is supplied to a memory unit in the form of a flip-flop 83 generating an output signal which starts a timer 84 providing an output signal at predetermined time intervals, for example for each 4.7 seconds, corresponding to the residence time of each of the optical filters 46 in the infrared radiation beam generated by the source 26. The output pulses of the timer 84 control a 4-bit decade down counter 85. The codes generated by the counter 85 are passed to a first comparator 86 for controlling the electric motor 38 of the filter change wheel 37 in response to signals received from the filter code device 43. The codes generated by the counter 85 are also passed to a second comparator 87 and to an operational control 88. The comparator 87 serves to stop the procedure when a program corresponding to that selected by the push buttons 82 has been passed. The operational control 88 controls the function of various devices of the apparatus. When the start signal has been received the operational control 88 starts the high pressure pump 70 and lights an operation indicating lamp 89 (FIG. 1) indicating that the measuring procedure has started. The comparator 86 checks whether the filter change wheel 37 is in its starting position, i.e. in the position in which the optical component filter WC for measuring water is in the radiation beam emitted by the radiation source 26. If not, the motor 38 is started in order to rotate the filter change wheel 37 to that position. During the first two steps of the counter 85 the milk sample is passed into the cuvette 24 as explained above and the milk in the cuvette obtains the desired temperature. The temperature conditions of the milk may be indicated by an indicating lamp 89a (FIG. 1). During the next step the optical reference filter FR for measuring fat is moved into the radiation beam, and a corresponding reference signal is generated by the detector 35. After a time period of b 4.7 seconds determined by the timer 84 the comparator 86 starts the motor 38 to move the component filter FC for measuring fat into the radiation beam. The detector 35 will now generate a corresponding component signal, and these detector signals will be processed as described below. Similarly, reference and component filters for protein, lactose, and water may successively be positioned in the radiation beam in accordance with the program selected, and corresponding signals will be generated by the detector 35.

Each detector signal is amplified by a preamplifier 90 arranged at the base of the detector (FIG. 2). The preamplified detector signals corresponding to the various sample components are further amplified in a gain set 91 at fixed programmed gains controlled by the operational control 88. The output of the gain set 91 is supplied to a filter 92 for selective transmission of signals at the frequency of the chopper 32 so as to amplify the signal and remove noise therefrom. The sinusoidal output signal from the filter 92 is rectified in an AC/DC converter 93 which converts the signal into a pulse DC voltage signal which is passed through a low-pass filter or a ripple filter 94 for reducing the ripple of the signal. The resulting signal from the low-pass filter is supplied to an electronic servocircuit 95 which is able to calculate the ratio of an input voltage signal to a succeeding voltage signal, viz. a reference signal, and the succeeding corresponding component filter as will be described more in detail below with reference to FIG. 8. The signal resulting from the calculation made in the circuit 95 is supplied to a first memory which is controlled by the control circuit 88. As the measurement made on the various components have not been made with reference to a natural zero level the output voltage is divided (multiplied by $\beta$ of the above expression) by means of "zero" potentiometers 98, and a fixed bias $(-\alpha_o)$ is added in a zero set circuit 97 so as to make the resulting voltage zero when the sample in the cuvette 24 is pure water. The potentiometers 98 which comprise a potentiometer for each of the components fat, protein, lactose, and water may be adjusted by means of zero adjusting knobs 98a on the keyboard 91 of the apparatus (FIG. 1). Prior to the actual measurement the knobs 98a have been adjusted so as to obtain the measuring result zero for each of the said components when the cuvette 24 contains pure water. The control circuit 88 selects the potentiometer corresponding to the component for which a signal is being treated.

The output signal from the memory 96 is supplied to a linearity set circuit 99 for individual linearity control for each of the components to be measured. The circuit 99 is controlled by the control circuit 88 and its setting is adjustable. The circuit 99 is connected to a logarithmic converter 100, and the converted signal is supplied to a gain set circuit 101 having potentiometers 102 which are adjustable by means of adjusting knobs 102a on the keyboard 81 (FIG. 1). The selection of the respective adjusted potentiometers is controlled by the control circuit 88. The purpose of this last mentioned gain setting is to obtain the same scale in the readout as the chemical standard values. The output of the circuit 101 is provided to a second memory 103 including a channel for each component to be measured and an adjusting potentiometer for intercorrelation of the channels. The memory also includes an adjustable potentiometer constituting a dummy lactose value to be introduced when a program including measurement of fat and protein, but not lactose has been selected by the push buttons 82. The memory 103 is controlled by the control circuit 88. The output signal from the memory 103 is added by a sum amplifier 104 including a mineral bias potentiometer which is adjustable by means of an adjusting knob 105 on the keyboard 81. The amplifier 104 is controlled by the control circuit 88, and the mineral bias is inserted when "total solids" and "total solids excluding fat" are calculated and read out. An analog/digital converter 106 converts the signals from the amplifier 104 into digital codes and generates a read out command to a display 107 and/or to a print out device (not shown) through an output interface circuit 108.

During calibration of the apparatus on water the signals from the logarithmic converter 100 may be supplied directly to the A/D converter 106 via a non-calibrated read out circuit 109 so that the result will now be independent of the adjustment of the gain set circuit 101 and of the memory 103. Various calibration modes may be selected by means of push buttons 82a and 82b of the keyboard 81.

Figure 8:
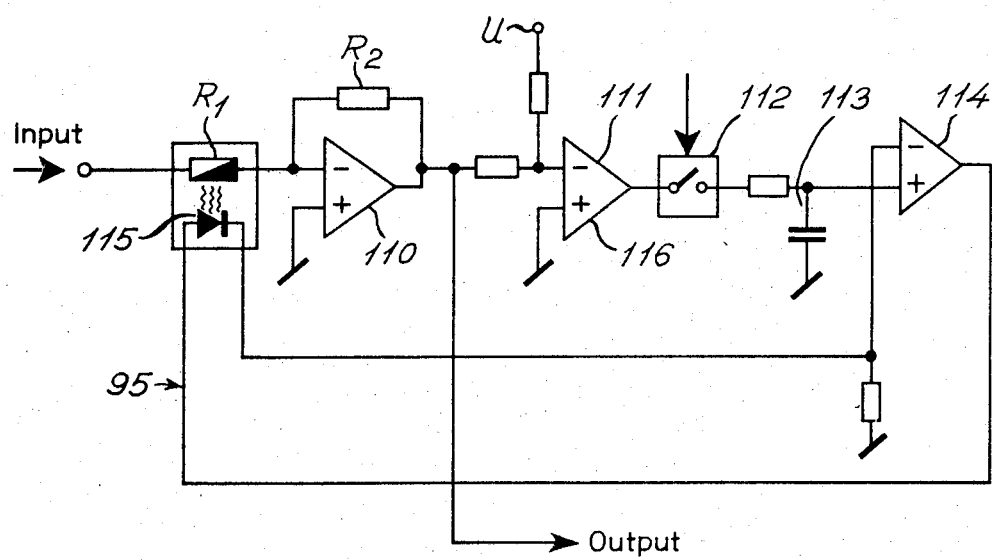
FIG. 8 shows a circuit of the electronic system more in detail.

The electronic servocircuit shown in FIG. 8 comprises a variable gain amplifier 110 including a variable resistor $R_1$ and a feedback including a resistor $R_2$. The circuit 95 furthermore comprises a limit sensor 111, a switching device 112 controlled by the control circuit 88, a memory 113, and an amplifier 114 the output of which is connected to a light emitting diode 115 controlling the variable resistor $R_1$, which may further comprise a photoresistor. A constant comparation voltage U is supplied to the input of an amplifier 116 included in the limit sensor 111.

When the input of the circuit 95 receives a reference signal $U_R$ the switching device 112 is closed. Therefore, the variable gain of the amplifier 110 will find a level at which the output voltage of the amplifier is equal to the comparation voltage U. Consequently, the resulting gain of the amplifier is $$G=(U/U_R)$$

This gain is maintained by the memory 113. When the following corresponding component voltage signal $U_C$ is supplied to the input of the circuit 95 the switching device 112 is opened by the control circuit 88, but the memory 113 still maintains the gain of the variable amplifier 110 previously set by the reference signal. Consequently, the signal provided at the output of the circuit 95 will be equal to $$U_C \cdot G = (U_C/U_R) \cdot U$$

It should be understood that the circuit 95 can be used not only in connection with the apparatus described above, but in any case where it is desired to determine the ratio between two successive signals. It should also be understood that various amendments and modifications of the apparatus described above could be made within the scope of the present invention. As an example, the apparatus could be used for measuring other liquid samples of milk and for determining any components thereof.

We claim:

1. An apparatus for measuring components of a liquid sample, said apparatus comprising
   (a) a source of infrared radiation,
   (b) transparent sample receiving means,
   (c) means for directing a beam of radiation from said source through said sample receiving means,
   (d) means for chopping said beam at a predetermined frequency and at a position between said source and said sample receiving means,
   (e) a plurality of pairs of optical filters, each of said pairs being associated with a respective one of said components and comprising a component filter for passing infrared radiation at a narrow frequency band at which the radiation absorbing ability of said component is relatively high, and a reference filter for passing infrared radiation at a different narrow frequency band at which the radiation absorbing ability of said component is low,
   (f) means for successively positioning said filters of at least one pair in said radiation beam between said source and said sample receiving means and for maintaining each filter in said radiation beam for a period of time exceeding 0.5 second and comprising a plurality of cycles of said chopping means,
   (g) a thermopile radiation detector arranged so as to receive radiation having passed said sample receiving means and for providing a signal in each said period of time in response to the radiation received, and
   (h) means for calculating values of the component associated with said one pair of filters on the basis of two said signals related to said one pair of filters.

2. An apparatus according to claim 1, wherein said chopping means are arranged between said source and said filters.

3. An apparatus according to claim 2, wherein said thermopile detector is of a monolithic type.

4. An apparatus according to claim 2, said apparatus being adapted to analyze samples of liquid milk products.

5. An apparatus according to claim 4, wherein the frequency bands of said filters are within the frequency range 4.5μ–10μ.

6. An apparatus according to claim 2, wherein said source, said sample receiving means, and said detector are aligned.

7. An apparatus according to claim 6, further comprising oppositely directed first and second concave mirrors, said infrared radiation source being arranged in front of said first mirror so as to focus the beam of radiation from said source on said sample receiving means and said detector being arranged in front of said second mirror so as to focus said radiation beam having passed said sample on said detector.

8. An apparatus according to claim 7, wherein said beam directing means define between said sample receiving means and said second mirror a radiation beam diverging at an angle of 20°–45°.

9. An apparatus according to claim 1, further comprising temperature control means for independently controlling the temperature of said filters.

10. An apparatus according to claim 1, wherein said detector provides signals representative of the amounts of radiation energy $E_c$ and $E_r$ received in the periods of time in which the component filter and the reference filter, respectively, of said pair of filters are maintained in said radiation beam, said calculating means being adapted to calculate a value C of the component on the basis of the expression $$(E_c/E_r)\beta - \alpha_o$$

wherein $\beta$ and $\alpha_o$ are predetermined constants.

11. An apparatus according to claim 10, wherein said calculating means comprise a variable gain amplifier, means for passing said $E_r$ signal to the input of the amplifier, means for varying the gain of said amplifier to a level at which the amplified $E_r$ signal corresponds to a predetermined value, means for maintaining the gain of the amplifier substantially at said level, and means for passing said $E_c$ signal to the input of the amplifier while the gain thereof is kept at said level.

12. An apparatus according to claim 11, wherein said gain varying means comprise a radiation sensitive resistor connected to the input of said amplifier, and a radiation emitting device controlled by the output of said amplifier.

13. An apparatus according to claim 12, wherein said gain maintaining means comprise a memory connected to the output of said amplifier and to said radiation emitting device and a switching device for disconnecting said amplifier and said memory while said $E_c$ signal is being passed to said amplifier.

14. An apparatus according to claim 2, further comprising filter selecting means for selecting one of a predetermined number of combinations of said plurality of filter pairs to be used for measuring selected components of a sample positioned in said sample receiving means, and for controlling the function of said filter positioning means in correspondence with the selection made.

15. An apparatus according to claim 14, wherein said filters are arranged on a rotatable filter supporting means, said filter selecting means comprise code markings connected to said rotatable filter supporting means, and code reading means arranged opposite to said code markings.

16. An apparatus according to claim 15, wherein said code markings comprise holes defined in a disc member and said code reading means comprising photoelectric sensors and corresponding light sources arranged on opposite sides of said disc member.

17. An apparatus according to claim 15, further comprising a mechanical locking device for locking said filter supporting means in a selected rotational position.

18. An apparatus according to claim 14, wherein said angle is 30°–40°.

19. An apparatus according to claim 2, wherein said filters are arranged on a filter support rotatable about an axis substantially parallel with the longitudinal axis of said beam.

20. An apparatus according to claim 19, wherein at least one of said filters is mounted adjustably on said support so that the angle defined between the axis of said support and the plane of said filter may be changed.

21. An apparatus according to claim 20, wherein said one filter is mounted in an annular holder defining a plane surface part forming an acute angle with the plane of said filter and engaging with a corresponding plane surface part on said support, said last-mentioned surface part forming with the axis of said support an angle being substantially a complement to said acute angle, said filter being adjustable by turning said holder in relation to said support.

22. An apparatus for measuring components of a liquid sample, said apparatus comprising
   (a) a source of infrared radiation,
   (b) transparent sample receiving means,
   (c) means for directing one beam of radiation from said source through said sample receiving means,
   (d) means for chopping said beam at a predetermined frequency and at a position between said source and said sample receiving means,
   (e) a plurality of pairs of optical filters, each of said pairs being associated with a respective one of said components and comprising a component filter for passing infrared radiation at a narrow frequency band at which the radiation absorbing ability of said component is relatively high, and a reference filter for passing infrared radiation at a different narrow frequency band at which the radiation absorbing ability of said component is low,
   (f) means for successively positioning said filters of at least one pair in said radiation beam between said source and said sample receiving means and for maintaining each component filter and each reference filter in said radiation beam in a period of time exceeding 1.5 seconds and comprising a plurality of cycles of said chopping means,
   (g) a thermopile radiation detector arranged so as to receive radiation having passed said sample receiving means and for providing a pulsed component signal in response to radiation received through the component filter of a pair of filters in one such period of time, and for providing a pulsed reference signal in response to radiation received through the reference filter of said pair in another such period of time, and
   (h) means for calculating a value of the component associated with said pair of filters on the basis of said component and reference signals.

23. An apparatus according to claim 22, said apparatus being adapted to analyze a sample of liquid milk products.

24. An apparatus according to claim 23, wherein the frequency bands of said filters are within the frequency range $4.5\mu$-$10\mu$.

25. An apparatus according to claim 23, wherein said source, said sample receiving means, and said detector are aligned.

26. An apparatus according to claim 25, further comprising oppositely directed first and second concave mirrors, said infrared radiation source being arranged in front of said first mirror so as to focus the beam of radiation from said source on said sample receiving means and said detector being arranged in front of said second mirror so as to focus said radiation beam having passed said sample on said detector.

27. An apparatus according to claim 22, wherein said thermopile detector is of a monolithic type.

28. An apparatus according to claim 23, wherein component and reference signals provided by said detector are representative of the amounts of radiation energy $E_c$ and $E_r$ received in periods of time in which the component filter and reference filter, respectively, of said pair of filters are maintained in said radiation beam, said calculating means being adapted to calculate a value C of the component on the basis of the expression $$(E_c/E_r)\beta - \alpha_o$$

wherein $\beta$ and $\alpha_o$ are predetermined constants.

29. An apparatus according to claim 23, wherein said chopping means are arranged between said source and said filters.

30. An apparatus according to claim 29, further comprising temperature control means for independently controlling the temperature of said filters.

31. An apparatus according to claim 23, further comprising filter selecting means for selecting one of a predetermined number of combinations of said plurality of filter pairs to be used for measuring selected components of a sample positioned in said sample receiving means, and for controlling the function of said filter positioning means in correspondence with the selection made.

32. An apparatus according to claim 31, wherein said filters are arranged on a rotatable filter supporting means, said filter selecting means comprising code markings connected to said rotatable filter supporting means, and code reading means arranged opposite to said code markings.

33. An apparatus according to claim 32, wherein said code markings comprise holes defined in a disc member and said code reading means comprise photoelectric sensors and corresponding light sources arranged on opposite sides of said disc members.

34. An apparatus according to claim 31, further comprising a mechanical locking device for locking said filter supporting means in a selected rotational position.

35. An apparatus according to claim 26, wherein said beam directing means define between said sample receiving means and said second mirror a radiation beam diverging at an angle of 20°-45°.

36. An apparatus according to claim 35, wherein said angle is 30°-40°.

37. An apparatus according to claim 22, wherein said calculating means comprise a variable gain amplifier, means for passing said reference signal to the input of the amplifier, means for varying the gain of said amplifier to a level at which the amplified reference signal corresponds to a predetermined value, means for maintaining the gain of the amplifier substantially at said level, and means for passing said component signal to the input of the amplifier while the gain thereof is kept at said level.

38. An apparatus according to claim 37, wherein said gain varying means comprise a radiation sensitive resistor connected to the input of said amplifier, and a radiation emitting device controlled by the output of said amplifier.

39. An apparatus according to claim 38, wherein said gain maintaining means comprise a memory connected to the output of said amplifier and to said radiation emitting device, and a switching device for disconnecting said amplifier and said memory while said component signal is being passed to said amplifier.

40. An apparatus according to claim 22, wherein said filters are arranged on a filter support rotatable about an axis substantially parallel with the longitudinal axis of said beam.

41. An apparatus according to claim 40, wherein at least one of said filters is mounted adjustably on said support so that the angle defined between the axis of said support and the plane of said filter may be changed.

42. An apparatus according to claim 41, wherein said one filter is mounted in an annular holder defining a plane surface part forming an acute angle with the plane of said filter and engaging with a corresponding plane surface part on said support, said last-mentioned surface part forming with the axis of said support an angle being substantially a complement to said acute angle, said filter being adjustable by turning said holder in relation to said support.

* * * * *